Figure 1:
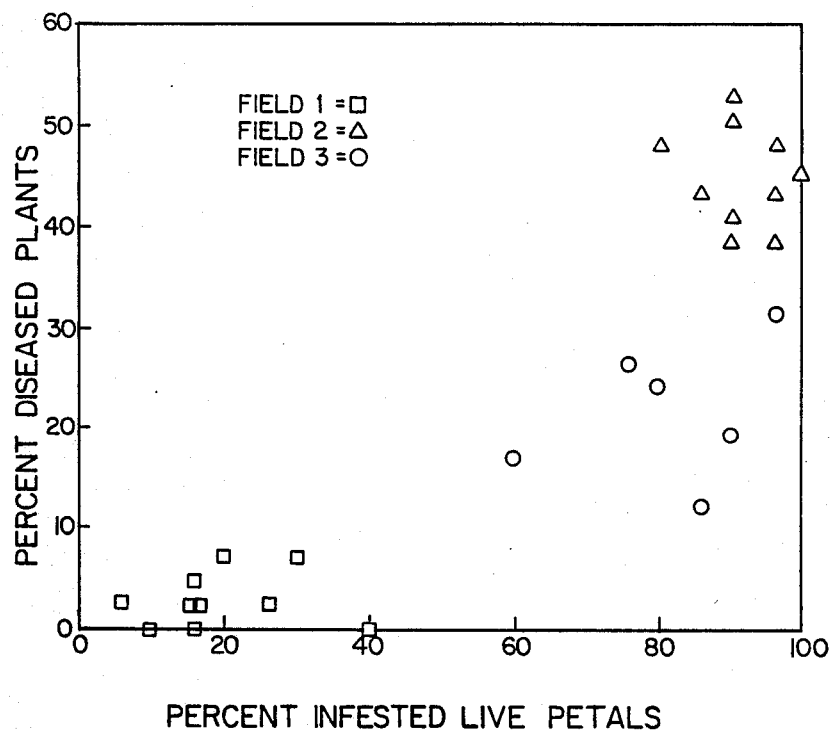

United States Patent [19]

Morrall et al.

[11] Patent Number: 4,837,146

[45] Date of Patent: Jun. 6, 1989

[54] FORECASTING THE RISK OF SCLEROTINIA STEM ROT IN CROPS

[75] Inventors: Robin A. A. Morrall; T. K. Turkington; Richard K. Gugel, all of Saskatoon; Sheldon V. Rude, Canwood, all of Canada

[73] Assignee: Canadian Patents & Development Ltd., Ottawa, Canada

[21] Appl. No.: 50,330

[22] Filed: May 18, 1987

[51] Int. Cl.$^4$ .......................... C12Q 1/02; C12Q 1/04; C12N 1/14

[52] U.S. Cl. ........................................ 435/34; 435/29; 435/39; 435/242; 435/254

[58] Field of Search ...................... 435/29, 34, 39, 254, 435/242

[56] References Cited

U.S. PATENT DOCUMENTS

| | | | |
|---|---|---|---|
| 2,437,766 | 3/1948 | Stevenson et al. | 435/254 |
| 4,456,684 | 6/1984 | Weller et al. | 435/243 X |
| 4,489,161 | 12/1984 | Papavizas | 435/254 |
| 4,594,323 | 6/1986 | Csonka et al. | 435/253 X |
| 4,636,386 | 1/1987 | Anderson et al. | 435/243 X |

Primary Examiner—Robert J. Warden
Assistant Examiner—Richard W. Wagner
Attorney, Agent, or Firm—Alan A. Thomson

[57] ABSTRACT

Sclerotinia stem rot, caused by the fungus *Sclerotinia sclerotiorum* (L ib.) de Bary, is a major disease of rapeseed (canola) in western Canada and many other parts of the world. Significant yield losses result from severe crop infestatons. A method of stem rot disease forecasting is disclosed. The method is based on the relationship discovered between infestation of top plant parts with spores of the fungus at early bloom and subsequent disease incidence. Also disclosed are media compositions, which facilitate rapid growth of *S. sclerotiorum* from plant parts under non-sterile conditions and thereby permit detection of the fungus. This forecasting system allows improved disease risk assessement in advance of the need for spraying against sclerotinia stem rot.

10 Claims, 1 Drawing Sheet

FORECASTING THE RISK OF SCLEROTINIA STEM ROT IN CROPS

BACKGROUND AND PRIOR ART

This invention relates to a method for forecasting stem rot disease of rapeseed (*Brassica napus* or *B. campestris*) caused by the fungus *Sclereotinia sclerotiorum* (Lib.) de Bary and to media compositions used in this forecasting assay.

The major features of the *S. sclerotiorum* life cycle in western Canada are the following. The fungus produces resting structures (sclerotia) in and on diseased plants. These structures overwinter with plant residues at or near the soil surface and can persist several years in the soil. In late June or early July the resting structures germinate if they are exposed to suitable conditions of moisture and temperature. Adequate moisture is generally available only when a sufficiently dense plant canopy has developed. The canopy provides permanent shading of the soil which allows the surface to remain moist for at least several days at a time. Germination of the resulting structures produces mushroom like structures (apothecia) that in turn release spores (ascospores). The spores become airborne and may travel hundreds of metres in the wind.

The spores can infect susceptible plants, such as rapeseed, but only if they are provided with nutrients from dead organic material on the plant surface. Normally in rapeseed crops, airborne spores are deposited on petals in situ in the inflorescence; the petals are ephemeral and after a few days fall from the inflorescence, carrying spores with them. If the contaminated petals land on rapeseed leaves or lodge in leaf axils, and if adequate moisture is available, the fungus colonizes the fallen petals and then penetrates the plant surface and initiates an infection. The fungus spreads in the stem, causing rotting, bleaching and weakening, resulting in shrivelled seeds, premature ripening and lodging in the crop.

Control of sclerotinia stem rot with only a single fungicide application during flowering is possible because of the unique role of flowering in the disease cycle. Before flowering the crop is usually not sufficiently dense to provide the right moisture conditions at the soil surface for spores to be released. Before and after flowering, dead petals are not available on plant surfaces to promote spore germination and infection. Thus protection of the crop throughout the entire growing season is unnecessary.

Application of the fungicides used to control sclerotinia stem rot is expensive, and since all crops do not automatically become infected, there is no need for systematic spraying. Farmers need to identify crops that are at high risk of infection; however, they cannot wait until diseased plants are evident in the crop. Disease does not appear until the crop is in late bloom and by then spraying is useless. Thus, there is great interest in an effective method of forecasting disease when the crop is in the early flowering stage so that a decision whether to invest in chemical control can be made.

Historically, disease forecasting systems have been host-, pathogen- or weather-oriented or have employed some combination of these three factors (Fry, W.E., 1982, Principles of plant disease management, Academic Press, N.Y., 378 pp.; Zadoks, J.C., 1984, Plant Dis. 68: 352–355). A forecasting system employing an arbitrary scale of points has been developed in western Canada for management of stem rot of rapeseed (Thomas, P.M., 1984, Canola Growers Manual, Canola Council of Canada, Winnipeg, Manitoba, p. 1053–1055). Points are awarded for qualitative measures of crop history, crop density, potential yield, probable degree of lodging, soil moisture, presence of water in the crop canopy, weather conditions before and during bloom, and the presence of apothecia in and around the field. Fungicide application is deemed necessary if the total number of points assigned exceeds a predetermined threshold (Thomas, P.M., 1984, op.cit.). While this system provides some assessment of disease risk, it does not allow quantitative disease prediction. Provided inoculum levels could be effectively monitored, the addition of a quantitative inoculum density-disease incidence (IDDI) relationship to this forecasting system would improve its accuracy and, when combined with reliable yield loss data (Morrall et al, 1984, Can. J. Plant Pathol. 6: 265), provide an estimate of the potential dollar loss.

Recent studies in eastern Canada demonstrated significant relationships between apothecium density and disease incidence in large (105 $m^2$) plots of white bean and soybean (Boland, G.J., 1984, Ph.D. Thesis, University of Guelph, Guelph, Ontario; Boland, G.J. and Hall, R., 1982, Can. J. Plant. Pathol. 4: 304; Boland, G.J. and Hall, R., 1983, Can. J. Plant Pathol. 5: 201). However, apothecium monitoring is not practical in non-row crops like rapeseed, especially on a large scale, because of the destructive sampling required. Furthermore, no clear IDDI relationships have yet been demonstrated for sclerotinia stem rot of rapeseed. W. Kruger's (Z. Pflanzenkrankh. Pflanzensch. 82: 101–108, 1975) statement that epidemics in winter rapeseed fields in Germany require the development of at least 3 apothecia/$m^2$ under favourable infection conditions probably does not apply to spring rapeseed in western Canada; Morrall and Dueck (Can. J. Plant Pathol. 4: 161–168, 1982; Proc. 6th Int. Rapeseed Conf., Paris, France, 957–962, 1983) have reported severe infestations in fields with few or no apothecia. The role of extrinsically-produced ascospores in causing disease in rapeseed fields may, therefore, be of considerable importance (Hims, M.J., 1979, Plant Pathol. 28: 197–198; Morrall, R.A.A. and Dueck, J., 1982, op.cit.; Morrall, R.A.A. and Dueck, J., 1983, op.cit.; Williams, J.R. and Stelfox, D., 1979, Plant Dis. Rep. 63: 395–399; Williams, J.R. and Stelfox, D., 1980, Can. J. Plant Pathol. 2: 169–172). Accordingly, ascospore concentrations above the crop canopy and on plant surfaces might reflect the disease potential in a crop better than the density of apothecia in the field.

The improved disease forecasting system we have developed depends on a quantitative assessment of the frequency of infestation of rapeseed petals with ascospores of *S. sclerotiorum* when the crop is in early bloom. By collecting petals from several parts of a field and determining the frequency of infestation with *S. sclerotiorum*, it is possible to forecast whether the risk of disease in the crop is low, moderate or high. The actual disease outcome in the crop will depend, of course, on environmental factors that influence the process of plant infection. However, it is possible to identify fields that are at low risk, and thereby save the farmer unnecessary expensive fungicide applications. This method has broader implications as detailed below.

SUMMARY OF THE INVENTION

According to the present invention there is provided a method of forecasting the incidence of plants in a crop infested with the stem rot fungus, *S. sclerotiorum*, in time to spray fungicides to control stem rot, comprising:
(a) sampling top plant parts from the typical crop plant, at an early bloom stage,
(b) inoculating the plant sample of (a) in a selected medium,
(c) incubating the inoculated medium (b) to allow the microorganisms to grow,
(d) screening the microorganisms for the presence of the stem rot fungus, S. sclerotiorum, and
(e) forecasting the probable disease incidence and need for spraying from the frequency of the stem rot fungus observed in the samples.

Further, according to the present invention, the top plant parts are selected from the group consisting of: live petals, dead petals, leaf axils and leaf bases, and in one preferred embodiment, the crop plant is rapeseed.

In some embodiments of the present invention the agar medium comprises a suitable carbon source, to allow for fungal growth, and antimicrobial agents, to inhibit bacterial growth but not fungal growth.

In one embodiment of the present invention, the nutrient medium comprises potato dextrose agar, about 5–40 ppm tetraiodotetrachlorofluorescein sodium salt and about 5–75 ppm streptomycin sulfate and the incubation step requires about 5 days or less at 22°–26° C.

In the preferred embodiment of the present invention, the nutrient medium comprises potato dextrose agar, about 5–75 ppm streptomycin sulfate and about 5–50 ppm anhydrous ampicillin and the incubation step requires 3 ½–4 days or less, at 22°–26° C.

Further, according to the present invention, the screening for the presence of *S. sclerotiorum* is by visual inspection of the inoculated plates and identification of *S. sclerotiorum* from other fungi.

Further, according to the present invention, the nutrient medium comprises potato dextrose agar, about 25 ppm streptomycin sulphate and about 25 ppm anhydrous ampicillin. This is considered a particular preferred and novel composition.

According to the present invention, there is also provided a kit containing thin plates or dishes containing the nutrient medium and visual standards to aid in the identification of the stem rot fungus.

BRIEF DESCRIPTION OF FIGURES

FIG. 1 shows a scatter diagram of disease incidence against percentage *S. sclerotiorum*-infested live petals for three fields of rapeseed (*Brassica napus* cv. Westar) in early bloom. Petal samples were collected at growth stage 4.1–4.2 and disease incidence was determined at growth stage 5.3. (See Table 1 for growth stage definitions.)

DETAILED DESCRIPTION

This assay method comprises sampling top plant parts, and determining the frequency of infestation with stem rot fungus, *S. sclerotiorum.* Live or dead petals, leaf axils or leaf bases can be used to determine infestation. The live petals are collected about 5 day –6 days after the first yellow blossoms appear in the field. At this time the crop should be in stage 4.2 according to the scale in Table 1. The appropriate time for collecting petal samples is at what many growers would call 20% bloom (about 15 flowers open on the main stem). The number of petals collected from a field must be sufficient to obtain a representative sample, about 40 petals, from 5–10 different plants from each site. Dead petals are collected from leaf surfaces and leaf axils, the most common infection courts. Leaf axils and leaf bases no higher than 40 cm from ground level are cut with scissors. As with the petals, leaf structures are sampled in sufficient numbers to provide a representative sample, about 10 from each site. The number of sites chosen per field (average field size is 30 hectares) is usually 4–10, preferably 4–6. It has been determined that a sample size of 4–6 sites per field, with 40 petals collected per site could be used to estimate the mean percentage of petals infested with a standard error of approximately 5%.

TABLE 1

| Canola Growth Stages |
|---|
| 0. Pre-emergence |
| 1. Seedling |
| 2. <u>Rosette</u> |
| 2.1 First true leaf expanded |
| 2.2 Second true leaf expanded |
| Add 0.1 for each additional leaf |
| 3. <u>Bud</u> |
| 3.1 Inflorescence visible at centre of rosette |
| 3.2 Inflorescence raised above level of rosette |
| 3.3 Lower buds yellowing |
| 4. <u>Flower</u> |
| 4.1 First flower open |
| 4.2 Many flowers opened, lower pods elongating |
| 4.3 Lower pods starting to fill |
| 4.4 Flowering complete, seed enlarging in lower pods |
| 5. <u>Ripening</u> |
| 5.1 Seed in lower pods full size, translucent |
| 5.2 Seed in lower pods green |
| 5.3 Seed in lower pods green-brown mottled |
| 5.4 Seed in lower pods brown |
| 5.5 Seed in all pods brown, plant senescent |

From Harper, F. R. and Berkenkamp, B., 1975, Can. J. Plant Sci., 55, 657–658.

Such a standard error would be acceptable in a practicle disease forecasting system because it would have a minor effect on forecasting relative to changes in the mean percentage of petal infestation with time. The sites are chosen at least 50 metres apart and 20–30 metres into the crop from the edge to avoid sampling where the stand is weedy or otherwise atypical.

Within six hours of collection all plant samples are plated on a sterile agar medium containing nutrients. Four petals are placed equidistant from each other in each petri dish. Leaf axils and leaf bases are trimmed with a scalpel and plated two per dish. An agar medium is chosen which will allow for growth of *S. sclerotiorum* such that it will outgrow most other fungi on the medium. Antibiotics are added to inhibit bacterial growth. The plates are incubated at room temperature (22° C.–26° C.) until the frequency of *S. sclerotiorum* can be scored.

A variety of different nutrient media have been used; however, the preferred medium is based on a potato dextrose agar. An example of such potato dextrose agar is supplied by Difco ® and contains per litre: infusion from 200 g of potatoes, 20 g of dextrose and 15 g of agar. Besides the carbon source, the medium also contains antimicrobial agents to inhibit bacterial growth but not fungal growth. It would be obvious to persons skilled in the art to choose an appropriate antimicrobial agent or a combination of more than one antimicrobial agents. The following is a list of antimicrobial agents and concentrations which have been tested and found to support growth of *S. sclerotiorum* comparable to the specific medium compositions disclosed in the Examples: norfloxacin, 5-50 ppm; ampicillin, 5-50 ppm; nalidixic acid, 5 ppm; tetracycline, 5-25 ppm; neomycin sulfate, 5-50 ppm; chloramphenicol, 5-50 ppm; streptomycin sulfate, 5-75 ppm; ampicillin, 25 ppm, and tetracycline, 5 ppm; ampicillin, 5-50 ppm, and streptomycin sulfate, 5-50 ppm; streptomycin sulfate, 25 ppm, and tetracycline, 5 ppm.

Disease incidence in each field is determined shortly before swathing. At each site the number of plants with one or more stem lesions is determined from a random sample of 100-200 plants and expressed as a percentage.

FIG. 1 shows a scatter diagram of disease incidence against percent of live petals infested with *S. sclerotiorum* for three rapeseed (*Brassica napus* cv Westar) fields. The petals were collected at growth stage 4.1-4.2 (see Table 1) and disease incidence was determined at ripening. Four sites were omitted from Field 3 because at those locations, the crop was atypically sparse. The three fields had different ranges of disease incidence with no overlap (Field 1, 0-8%; Field 3, 12-30%; Field 2, 38-52%) and they were arbitrarily classified as low, moderate and high, respectively. On this scale a general trend was evident in that low levels of infested petals were associated with low disease incidence, and moderate and high levels of infested petals with higher disease incidence. This relationship was strongest between the frequency of live petals at early bloom infested with *S. sclerotiorum* (growth stage 4.1-4.2) and disease incidence.

Live petals are much easier to collect and suffer less extraneous bacterial contamination on the isolation plates. Thus, it would be more practical to use live petals than dead petals as a basis for disease prediction. The leaf axils and leaf bases provided no additional useful information over the data collected from the petals.

Moreover, sampling of leaf axils or leaf bases or both would not be as practical as sampling petals in a disease management program because it would be more cumbersome and time-consuming. Furthermore, soil particles and other debris are often trapped by these plant structures resulting in more extraneous contamination of the isolation plates and, hence, greater difficulty in identifying *S. sclerotiorum*.

There are a number of environmental factors which affect the accuracy of this disease forecasting method. Total rainfall may be important to diseases like sclerotinia stem rot. The timing of the rainfall is also critical. Moisture is necessary at the time that dead infested rapeseed petals are present on leaves and in leaf axils; otherwise, *S. sclerotiorum* cannot grow out of the petals and into the leaves and stems.

Crop stand density will also affect the relationship between petal infestation with *S. sclerotiorum* and diseased plants. In a light stand, plant surfaces will dry quickly after rainfall and may prevent *S. sclerotiorum* growing from infested petals into the leaves and stems. There are many reasons for a light stand, for example, heavy growth of some types of weeds or severe blackleg disease. The opposite type of effect can also occur. Unusually dense stands which can maintain excessive moisture under the crop canopy may show more sclerotinia stem rot disease than expected from a given level of petal infestation.

Although the examples given demonstrate the method of disease forecasting of stem rot (*S. sclerotiorum*) in rapeseed, this method may be used on other plant crops susceptible to *S. sclerotiorum* infection, such as soybean or white bean.

EXAMPLES

The following specific examples are intended to illustrate more fully the nature of the present invention without acting as a limitation upon its scope.

Example 1

Plant parts from rapeseed (*Brassica napus* or *B. campestris*), preferably petals (approximately 40), are collected from a minimum of 4-6 sites in a field. Four petals are placed equidistant from each other in a 9 cm petri dish containing 15 ml Difco ® potato dextrose agar, prepared according to the manufacturer's instruction, containing 40 ppm Rose Bengal ® (Sigma Chemical Co.) (tetraiodotetrachlorofluorescein sodium salt, an antimicrobial agent), and 30 ppm streptomycin sulfate. Following 11 days incubation at room temperature (22° C.-26° C.), preferably at 25° C., the presence of *S. sclerotiorum* is scored by visual inspection of the plates and the percentage frequency of petals infested with spores is calculated.

Table 2 shows the relationship between the frequency of petal infestation and the probable loss in yield. As discussed previously, forecasting the probable percentage of diseased plants in the crop is the most variable because of the environmental factors that affect the development of the disease. Thus if hot dry weather occurs during late bloom the actual percentage of diseased plants and percent yield loss in a crop will be less than forecast. Conversely, if unusually cool wet weather persists during late bloom, even fields at low risk may develop moderate amounts of sclerotinia stem rot.

TABLE 2

| | 0%–45% | 45%–90% | 90%–100% |
|---|---|---|---|
| (1) % FREQUENCY OF PETALS INFESTED WITH SPORES AT EARLY BLOOM ↓ | | | |
| (2) RISK OF DISEASE ↓ | LOW | MODERATE | HIGH |
| (3) PROBABLE % OF DISEASED PLANTS IN THE CROP ↓ | 0%–20% | 20%–40% | 40%–55% |
| (4) PROBABLE % LOSS IN YIELD ↓ | 0%–10% | 10%–20% | 20%–28% |
| BUSHEL LOSS | WILL DEPEND ON YIELD POTENTIAL OF CROP | | |

TABLE 2-continued

```
    ⑤
     ↓              ↓        ↓        ↓
$ LOSS IF CROP    WILL DEPEND ON MARKET
 NOT PROTECTED        PRICE OF CANOLA
   BY SPRAYING
```

Example 2

In assessing the risk of stem rot infection, time is of the essence. Forecasting the probable disease incidence must be done in the short period of time when the crop is between early and full bloom. Otherwise, by the time a result is obtained, the crop is past the stage at which foliar fungicide application for disease control will be effective. The time it takes for *S. sclerotiorum* to grow on the plates has been decreased by modifying the composition of the agar medium used for plating the petals.

In this Example the samples (petals) are collected and plated as in Example 1. However, the agar medium comprises: Difco ® Bacto-Potato dextrose agar, 20 ppm Rose Bengal ® and 30 ppm streptomycin sulfate. On this medium the presence of *S. sclerotiorum* is scored after 5 days incubation at 22°-26° C., preferably at 25° C. The same forecasting table (Table 2) is used to predict the probable loss in yield.

Example 3

In this Example the samples (petals) are collected and plated as in Example 1. The agar medium comprises: Difco ® Bacto-Potato dextrose agar, 25 ppm streptomycin sulfate and 25 ppm anhydrous ampicillin. On this medium the presence of *S. sclerotiorum* is scored after 3 ½-4 days incubation at 22°-26° C., preferably at 25° C. The probable percent loss in yield is predicted as in the previous Examples.

We claim:

1. A method of forecasting the incidence of diseased plants in a rapeseed or canola crop, the disease being the stem rot fungus, Sclerotinia sclerotiorum, therefore comprising:

(a) selecting and sampling top non-stem plant parts from typical rapeseed or canola plants, at an early bloom stage before the disease becomes visible;

(b) inoculating the plant sample of a) in a selective medium which favours germination of spores and growth of said stem rot fungus while inhibiting most other microorganisms;

(c) incubating the inoculated medium of (b) to allow the microorganisms to grow;

(d) screening the microorganisms for the presence of the stem rot fungus in each sample; and (e) forecasting the probable disease incidence and need for spraying a fungicide to control the disease from the frequency of the stem rot fungus observed in the samples.

2. The method according to claim 1 wherein the plant parts of (a) are selected from the group consisting of live petals, dead petals, leaf axils and leaf bases.

3. The method according to claim 1 wherein the plant parts of (a) are live petals.

4. The method according to claim 1 wherein the agar medium comprises a suitable carbon source to allow fungal growth, and anitmicrobial agents to inhibit bacterial growth but not fungal growth.

5. The method according to claim 1 wherein the agar medium of step (b) comprises potato dextrose agar, and bacterial but non-fungicidal amounts of tetraiodotetrachlorofluorescein sodium salt and streptomycin sulfate.

6. The method according to claim 1 wherein the agar medium of step (b) comprises potato dextrose agar, about 5-40 ppm tetraiodotetrachlorofluorescein sodium salt, and about 5-75 ppm streptomycin sulfate.

7. The method according to claim 1 wherein the agar medium of step (b) comprises potato dextrose agar, about 5-75 ppm streptomycin sulfate and about 5-50 ppm anhydrous ampicillin.

8. The method according of claim 1 wherein the incubation step of (c) is performed at 22° C.-26° C.

9. The method according to claim 1 wherein the incubation step of (c) is performed at 25° C.

10. The method according to claim 1 wherein the screening for the presence of *S. sclerotiorum* is by visual inspection of the plates and distinguishing between *S. sclerotiorum* and other fungi.

* * * * *

UNITED STATES PATENT AND TRADEMARK OFFICE
CERTIFICATE OF CORRECTION

PATENT NO. : 4,837,146,

DATED : June 6, 1989

INVENTOR(S) : Robin A.A. Morrall et al

It is certified that error appears in the above-identified patent and that said Letters Patent is hereby corrected as shown below:

Column 1, line 8, correct spelling of "Sclerotinia"

Column 1, line 23, "the resulting structures" should read --the resting structures--.

Signed and Sealed this

Eighth Day of May, 1990

Attest:

HARRY F. MANBECK, JR.

*Attesting Officer*   *Commissioner of Patents and Trademarks*